(12) United States Patent
Paulen

(10) Patent No.: US 9,958,303 B2
(45) Date of Patent: May 1, 2018

(54) MEASURING DEVICE, UROLOGICAL INSTRUMENT AND RECEIVING DEVICE

(75) Inventor: Thomas Gijsbert Paulen, Eindhoven (NL)

(73) Assignee: IQ+ INVESTMENTS N.V., Curacao (NL)

( * ) Notice: Subject to any disclaimer, the term of this patent is extended or adjusted under 35 U.S.C. 154(b) by 494 days.

(21) Appl. No.: 12/999,418

(22) PCT Filed: Jun. 15, 2009

(86) PCT No.: PCT/NL2009/050339
§ 371 (c)(1),
(2), (4) Date: Mar. 23, 2011

(87) PCT Pub. No.: WO2010/005292
PCT Pub. Date: Jan. 14, 2010

(65) Prior Publication Data
US 2011/0166537 A1 Jul. 7, 2011

(30) Foreign Application Priority Data
Jun. 16, 2008 (NL) ..................................... 2001691

(51) Int. Cl.
*A61M 1/00* (2006.01)
*A61B 5/20* (2006.01)
*G01F 1/52* (2006.01)
(52) U.S. Cl.
CPC ................ *G01F 1/52* (2013.01); *A61B 5/208* (2013.01)
(58) Field of Classification Search
CPC ............ A61M 1/00; A61B 5/208; G01F 1/52

USPC ................................... 604/318, 319; 29/428
See application file for complete search history.

(56) References Cited

U.S. PATENT DOCUMENTS

| 3,859,854 A | 1/1975 | Dye et al. |
|---|---|---|
| 4,238,448 A | 12/1980 | Salvadori et al. |
| 4,241,017 A | 12/1980 | Balistreri et al. |
| 4,384,485 A | 5/1983 | Layton et al. |
| 2008/0041491 A1 | 2/2008 | Salani et al. |

FOREIGN PATENT DOCUMENTS

| DE | 24 47 261 A1 | 4/1976 |
|---|---|---|
| EP | 1 571 994 B1 | 10/2008 |
| FR | 2 420 507 A1 | 10/1979 |
| NL | 1 015 080 C2 | 11/2001 |
| WO | 2004/054446 A1 | 7/2004 |

OTHER PUBLICATIONS

International Search Report, dated Feb. 15, 2010, from corresponding PCT application.

*Primary Examiner* — Michele Kidwell
*Assistant Examiner* — Ilya Treyger
(74) *Attorney, Agent, or Firm* — Young & Thompson

(57) ABSTRACT

A measuring device 1 for recording a peak level of a liquid flow includes an inlet 2 which opens into an inlet chamber 3 for receiving the liquid flow and a recording chamber 4 in open liquid communication with the inlet chamber 3 for allowing the liquid flow to accumulate up to a level therein. The recording chamber 4 is separated from the inlet 2 for direct liquid communication. At least one outflow opening 9 is provided to allow at least partial escape of the liquid flow, and indicator elements are provided to leave an indication of a level at least approximately at an indication level. A peak level in a liquid flow can thus be recorded very reliably with the measuring device 1.

11 Claims, 2 Drawing Sheets

MEASURING DEVICE, UROLOGICAL INSTRUMENT AND RECEIVING DEVICE

The present invention relates to a measuring device for recording a peak level of a liquid flow, comprising an inlet for receiving the liquid flow and a recording chamber in open liquid communication with the inlet for allowing the liquid flow to accumulate at least temporarily up to a level, wherein at least one outflow opening is provided below an indication level to allow at least partial escape of the liquid flow, and wherein indicator means are provided to leave an indication of a level at least approximately at the indication level. In the present invention the peak level of the liquid flow must be understood to mean the at least approximately maximum inflow speed, calculated in volume per unit time, at which the liquid flow enters the instrument. The present invention also relates to a urological instrument for recording a peak level of a urine flow with a measuring device according to the present invention. The present invention further relates to a receiving device, comprising a substantially hollow receiving chamber inside a wall and open on both sides, wherein the wall can be expanded manually from a relatively flat storage state to an expanded, ready-to-use state in which the receiving chamber extends between a closed upper edge and a closed lower edge, and a cross-section enclosed by the upper edge is significantly larger than a cross-section enclosed by the lower edge.

BACKGROUND OF THE INVENTION

A urological instrument with a measuring device and receiving device as stated in the preamble is known from the European patent application EP 1571994. The receiving device of the known instrument comprises a wall with an upper edge and a lower edge, wherein a cross-section enclosed by the upper edge is significantly larger than a cross-section enclosed by the lower edge. The receiving device can be manually expanded here from a relatively flat storage state to an expanded ready-to-use state, wherein a hollow receiving chamber inside the wall is left clear. With the known receiving device a liquid can be readily received in the receiving chamber in the ready-to-use state. Measurement can then be performed on a received liquid using the measuring device. In the known instrument the measuring device comprises a recording chamber in which a liquid flow can accumulate up to a level and which is provided with at least one outflow opening to allow at least partial escape of the liquid flow. During use of the known device a liquid flow with a peak level higher than an outflow capacity, calculated in volume per unit time, out of the at least one outflow opening will thus accumulate in the recording chamber up to a level above the at least one outflow opening. Indicator means are provided to leave an indication hereof. A peak level of a volume flow can hereby be recorded using the known device.

Although the known urological instrument represents an innovative product with which a liquid flow can be received and a peak level thereof can be recorded very well, the known device does not always give an equally reliable result. The present invention has for its object, among others, to provide a measuring device of the type stated in the preamble which in at least substantially all cases records a peak level of a liquid flow in extremely reliable manner.

SUMMARY OF THE INVENTION

In order to achieve the stated object a measuring device of the type stated in the preamble has the feature according to the invention that the inlet opens into an inlet chamber, that the inlet chamber is in open liquid communication with the recording chamber and that the recording chamber is separated from the inlet for direct liquid communication. Owing to such a separation of the recording chamber and the inlet a liquid flow cannot flow directly out of the inlet into the recording chamber with the at least one outflow opening. This at least temporarily prevents a liquid escaping directly from the inlet through the at least one outflow opening. Since direct loss of at least a part of the liquid flow is prevented, the measuring device thus provides a very reliable recording of a peak level in a liquid flow.

A practical embodiment of the device of the present invention is characterized in that the inlet chamber and the recording chamber are situated at least substantially parallel to and adjacently of each other and are separated from each other by an intermediate wall, and that the intermediate wall leaves a passage opening on a side remote from the inlet.

In a preferred embodiment the device of the present invention is characterized in that the passage opening lies below the indication level. Because the passage opening lies below the indication level, during use of the device a liquid will first accumulate below the indication level in the recording chamber so that the indicator means then only leave an indication of a level approximately at the indication level when a sufficient quantity of liquid accumulates in the recording chamber. False indications are thus prevented.

In a further preferred embodiment the device of the present invention is characterized in that the recording chamber comprises a series of outflow openings in a longitudinal wall thereof, and that indicator means are provided at each of the outflow openings. At least a part of the liquid flow can escape at each outflow opening of the series so that for each outflow opening a determined peak level of the liquid flow is required in order to rise above the outflow opening in the recording chamber. Because indicator means are provided at each of the outflow openings, it is possible to read in simple manner up to which outflow opening the liquid flow has accumulated. A peak level of the liquid flow is thus recorded very precisely.

In a further preferred embodiment the device of the present invention is characterized in that the recording chamber is in open liquid communication with an outlet chamber via at least the at least one outflow opening. During use of the device a part of the liquid flow which has escaped from the at least one outflow opening can thus be discharged into the outlet chamber. In a particular embodiment the device of the present invention is characterized in that the longitudinal wall is sheet-like. Because the longitudinal wall is sheet-like, a flow resistance in the at least one outflow opening thereof will remain limited to a minimum. A liquid will thus flow without appreciable resistance out of the recording chamber through the at least one outflow opening into the outlet chamber.

A further preferred embodiment of the device of the present invention has the feature that the indicator means comprise a suitable indicator substance for the purpose of indicating a contact with a liquid. Such indicator means are available per se to a skilled person, and can thus be integrated in simple manner into the instrument according to the invention.

In an extremely practical embodiment the device of the present invention is characterized in that the indicator means are arranged on an inner wall of the recording chamber at the at least one outflow opening, and in a more particular embodiment the device of the present invention is characterized in that the indicator means comprise a surface accessible to liquid in an area between a longitudinal wall with the at least one outflow opening and a centre of a width line of the recording chamber. It has been found that, even in the case that use of the measuring device is not optimal, such as when the device is in a slightly tilted position, indicator means in this area can record a peak level of a liquid flow in extremely reliable manner.

In a further preferred embodiment the device of the present invention is characterized in that the indicator means comprise a flexible carrier, in particular paper, on which the indicator substance is arranged. The indicator substance can thus be readily arranged at one or more desired positions on the carrier. The flexible carrier moreover provides for easy placing thereof in the recording chamber.

In a further preferred embodiment the device of the present invention is characterized in that the indicator substance is attached to the carrier with a liquid-tight attaching means. The liquid-tight attaching means here prevents a liquid, in particular an absorption front of a liquid, coming into contact in the carrier with the indicator substance. Recording of a false peak level with the measuring device is thus prevented.

In a preferred embodiment the device of the present invention is characterized in that at least the recording chamber is bounded by at least one wall with at least a translucent window at least at the position of a recording range in the recording chamber. Such a wall leaves a free view of the recording range, thus enabling easy reading of a recording.

For an extra-precise and reliable recording of a peak level in a liquid flow a particular embodiment of the device of the present invention has the feature that the device is manufactured, at least around the at least one outflow opening, from a hydrophilic material. A liquid will hereby flow substantially unimpeded through the at least one outflow opening, so that a maximum outflow speed out of the at least one outflow opening can be precisely determined.

In a further preferred embodiment the device of the present invention is characterized in that the device comprises an at least substantially flat assembly of a first sheet-like structural part from which at least one transverse wall extends, by which at least the inlet, inlet chamber and recording chamber are bounded, and a second sheet-like structural part attached at least substantially liquid-tightly to the first structural part while enclosing the at least one transverse wall in at least substantially jointless manner. Such a measuring device can be manufactured in simple manner and at a relatively low cost price. In an extra-advantageous embodiment the device of the present invention is characterized in that at least one of the first structural part and the second structural part comprises a thermoformed part, in particular an injection moulded part.

A user-friendly embodiment of the urological instrument of the type stated in the preamble is characterized in that a substantially hollow receiving device for the urine flow is provided therein which narrows from a distal side with a receiving opening to a proximal side and which, at least during use, connects with the proximal side to the inlet of the measuring device. The receiving opening in the receiving device hereby has larger dimensions than the inlet of the measuring device. A liquid flow can thus be admitted easily, or at least substantially without waste, to the measuring device.

In a preferred embodiment the urological instrument of the present invention is characterized in that the receiving device has a first, relatively compact storage state and a second, expanded ready-to-use state, and that the receiving device is designed and adapted to be brought manually from the storage state to the ready-to-use state. In the storage state the instrument can thus be compact and convenient as a whole so that it can be easily carried by a user and held in stock. In order to be used the instrument can then be brought relatively easily and manually to a ready-to-use state by expanding at least the receiving member. A cavity is then present therein on at least one side for the purpose of receiving the urine flow therein.

In a further preferred embodiment the instrument of the present invention is characterized in that at least an upper edge of the receiving device is at least substantially form-retaining and is provided with an at least substantially form-retaining engaging part, that the receiving device and the engaging part are foldable along a shared first fold-line from the storage state to a transition state, and that the engaging part and the receiving device are mutually connected via a second fold-line for folding at least substantially transversely of the first fold-line in order to fix the receiving device in the ready-to-use state. The receiving device can thus be brought manually into a ready-to-use state and fixed in this state in very simple manner.

In a particular embodiment hereof the instrument of the present invention is characterized in that the engaging part comprises a gripping opening extending on either side of the first fold-line. The gripping opening provides a convenient point of engagement with which the instrument can be carried for a relatively long time. The first fold-line is moreover interrupted by engaging in the gripping opening, whereby the receiving device cannot automatically return to the storage state.

In a further preferred embodiment the instrument of the present invention wherein the measuring device is provided with an outlet chamber is characterized in that a collecting device is provided therein which, at least during operation, is in open communication with the outlet chamber of the measuring device, that the collecting device is provided distally with a closing member and that the collecting device is expandable from a relatively compact storage state to an expanded position of use. Owing to the presence of the collecting device the instrument can also be applied in situations where a sewer system or other drain is not immediately available. By operating the closing member the collecting device can be emptied later at an appropriate moment and/or suitable location. Because the collecting device is expandable, the above stated convenience of use and the compactness of the instrument is not adversely affected, or hardly so, at least in the storage state. During use the collecting device expands as it becomes further filled with urine.

In a further preferred embodiment the instrument of the present invention is characterized in that the collecting device is provided with volume indicator means for a urine volume received therein. Not only can the flow rate and magnitude of the urine flow be easily measured in this way, but it is also possible to measure the quantity of urine which serves as basis for the measurement to be performed using the instrument.

In a further aspect of the invention the instrument has the feature that the instrument is embodied as disposable article wherein, at least in the storage state, successive functional components thereof are folded over each other to form a relatively flat whole, and in the ready-to-use state lie at least substantially mutually in line. Such an instrument embodied as a disposable article is highly suitable for use in a modern environment such as a hospital, and is moreover very suitable for home use. After use of the instrument to measure the amount and optionally the quantity of the urine flow, the instrument is can be discarded with the hospital waste or domestic refuse. In the ready-to-use state the urine flow can flow through the instrument unimpeded along a substantially straight urine path, while the folded storage state provides the desired compactness.

The instrument according to the invention can be produced on large scale in relatively economic manner. For this purpose a particular embodiment of the instrument according to the invention has the feature that the measuring device is enclosed between a pair of foil sheets, which foil sheets are joined hermetically to each other on a mutual contact surface and at least partially form one or more components of the instrument. By glueing or sealing a pair of separate foil sheets for instance locally to each other, the one or more components of the instrument can be simultaneously formed therefrom in the same processing step.

It is also desirable in some cases, with a view to the final diagnosis to be made, to have information available about the overall urination time of the patient. In order to provide for this a further preferred embodiment of the instrument according to the invention has the feature that time duration indicator means are provided therein for determining a time duration of the urine flow.

A receiving device of the type stated in the preamble has the feature according to the invention that the wall of the receiving chamber adjacent to the upper edge comprises at least an edge part which is rigid and which extends at least substantially around the upper edge, and that the edge part is provided with an engaging member which is connected to the edge part for pivoting about an at least substantially straight pivot axis and which extends distally outside the upper edge. Engagement of the receiving device is simple here due to the engaging member.

In order to move the receiving device easily from the storage state to the ready-to-use state, the receiving device of the present invention is characterized in a preferred embodiment in that the engaging member and the at least edge part comprise a shared pivot axis substantially transversely of the upper edge and can be folded out about the shared pivot axis. Because the shared pivot axis lies substantially transversely of the straight pivot axis, the receiving device is moreover easy to fix manually in the ready-to-use state.

In a further preferred embodiment the receiving device of the present invention is characterized in that the engaging member comprises an engaging opening extending on either side of the shared pivot axis. The engaging opening provides a convenient point of engagement with which the instrument can be carried for a relatively long period of time. The shared pivot axis is moreover interrupted by engaging in the engaging opening, whereby the receiving device cannot return automatically to the storage state.

In a particular embodiment the receiving device of the present invention is characterized in that the engaging part extends integrally from the at least edge part and is separated from the edge part by a substantially linear weakening zone. In a further particular embodiment the receiving device of the present invention is characterized in that the wall adjacent to the upper edge comprises a strip-like, rigid edge part and a flexible foil at least from the edge part as far as the lower edge.

A further preferred embodiment of the receiving device of the present invention has the feature that the foil and the edge part comprise an at least mutually compatible plastic, in particular the same plastic, and are attached hermetically to each other, in particular are mutually sealed, in a mutually overlapping area. In a particular embodiment hereof the receiving device of the present invention is characterized in that the plastic comprises a plastic from a group comprising polyethylene, polypropylene, polyethylene terephthalate (PET) and polyester.

BRIEF DESCRIPTION OF THE DRAWINGS

The invention will be further elucidated hereinbelow on the basis of a number of exemplary embodiments and an associated drawing. In the drawing.

The figures are otherwise purely schematic and not drawn to scale. Some dimensions in particular may be exaggerated to a greater or lesser extent for the sake of clarity. Corresponding parts are designated as far as possible in the figures with the same reference numeral.

DETAILED DESCRIPTION OF THE PREFERRED EMBODIMENTS

Figure 1:
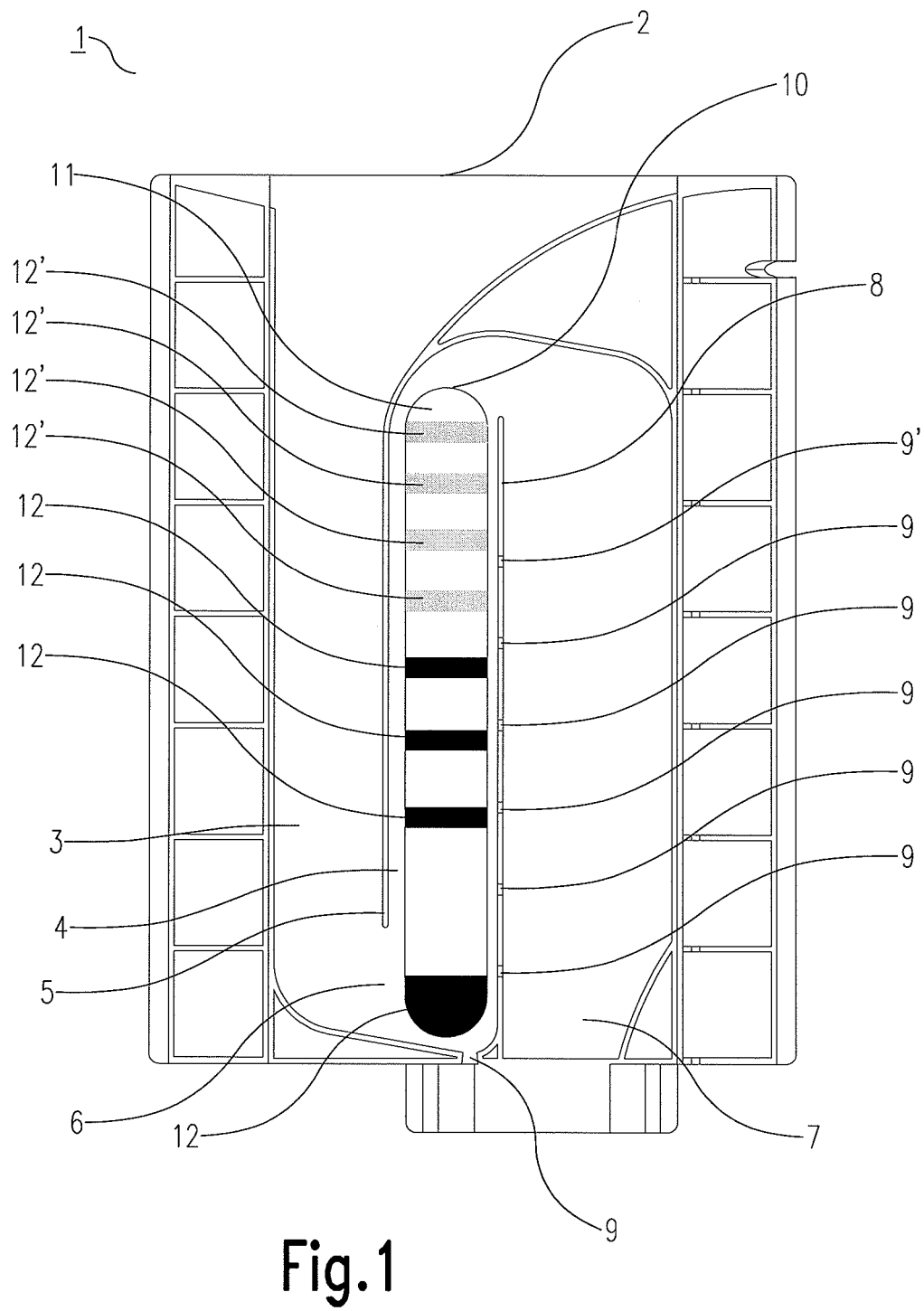
FIG. 1 shows a front view of an exemplary embodiment of a measuring device according to the invention.

FIG. 1 shows a front view of an exemplary embodiment of a measuring device according to the invention. As shown in FIG. 1, measuring device 1 comprises an inlet 2 in open liquid communication with an inlet chamber 3. A liquid flow admitted at inlet 2 will thus flow into inlet chamber 3 and at least temporarily accumulate up to a level therein. Inlet chamber 3 is situated at least substantially parallel to and adjacently of a recording chamber 4. Inlet chamber 3 and recording chamber 4 are here separated from each other by a sheet-like intermediate wall 5 but are in open liquid communication with each other on a side remote from the inlet through a passage opening 6 in intermediate wall 5. A liquid flow from inlet chamber 3 will hereby flow into recording chamber 4 and at least temporarily accumulate up to a level therein. Recording chamber 4 is separated from an outlet chamber 7 by a longitudinal sheet-like wall 8 in which there is at least one outflow opening, although in this exemplary embodiment a series of outflow openings 9, 9' are provided to allow a liquid flow in recording chamber 4 to at least partially escape therefrom. Liquid which escapes from recording chamber 4 through outflow openings 9, 9' is here discharged into the outlet chamber. In this exemplary embodiment the longitudinal wall 8 is sheet-like in order to minimize a resistance exerted on the liquid in outflow openings 9, 9'. The longitudinal wall can however optionally also be given a relatively thick form, wherein outflow openings 9, 9' form channels through the wall. In such an embodiment the liquid will meet with a greater resistance, so that the liquid will run less quickly out of the recording chamber. This effect is further reinforced when the material of the longitudinal wall around outflow openings 9, 9' has a certain hydrophobicity. In some cases it may be that the liquid meets with a resistance in openings 9, 9' such that the liquid in the recording chamber first rises above an opening 9, 9' before it can flow under liquid pressure out of openings 9, 9'. In order to prevent possible inaccuracies in a measurement resulting from such properties of outflow openings 9, 9' measuring device 1 can be calibrated prior to use. Tested here using predetermined flow speeds is the height to which a liquid flow associated with a determined flow speed accumulates in recording chamber 4.

During use of the plastic measuring device 1 a liquid flow admitted at inlet 2 will accumulate via inlet chamber 3 up to a determined level in recording chamber 4. At least a part of the liquid flow will here escape continuously from recording chamber 4 via at least a number of the outflow openings 9, 9'. The number of outflow openings 9, 9' through which the liquid escapes depends here on the level of the liquid in recording chamber 4. The higher a level of the liquid in recording chamber 4, the more outflow openings 9, 9' through which the liquid will escape from the recording chamber. A level of liquid in the recording chamber will only rise above a determined outflow opening if a peak level of the liquid flow is higher than an overall outflow capacity of outflow openings 9, 9' up to and with the determined outflow opening. If an overall outflow capacity of outflow openings 9, 9' up to and including the determined outflow opening is equal to or higher than a peak level of a liquid flow, the liquid in the recording chamber will then not rise above the determined outflow opening.

For the purpose of recording a peak level of a liquid flow indicator means 10 are provided in measuring device 1 at outflow openings 9, 9'. Indicator means 10 leave an indication, at least at an indication level, of a level of liquid in recording chamber 4. The indicator means comprise a flexible carrier 11 arranged on an inner wall of recording chamber 4. In this exemplary embodiment the flexible carrier 11 is a simple strip of paper 11. Bands of indicator substance 12, 12' are arranged on carrier 11 at the position of outflow openings 9, 9'. The bands of indicator substance 12, 12' discolour upon contact with a liquid so that, when a liquid in recording chamber 4 rises to a level the same as a band of indicator substance 12, 12', an indication is given hereof. In order to prevent a liquid, in particular an absorption front of a liquid, which migrates through the strip of paper 11, coming into contact with the indicator substance and herein possibly leaving a false peak level through discolouring of the indicator substance, the bands of indicator substance 12, 12' are attached to carrier 11 with a liquid-tight attaching means. Carrier 11 can however also be manufactured from a liquid-impermeable material, such as for instance a flexible sheet of plastic, or for instance be finished wholly with a liquid-impermeable layer, for instance a plastic foil, before the bands of indicator substance 12, 12' are arranged thereover, in order to prevent such a false indication.

As shown in FIG. 1, the lower four bands of indicator substance 12 on carrier 11 are discoloured, and the upper four bands of indicator substance 12' on carrier 11 are not discoloured. Indicator means 10 of FIG. 1 thus show that the liquid flow in the recording chamber has accumulated to a level at least approximately at an indication level of a fourth band of indicator substance 12. The peak level of the liquid flow here has at least approximately a value higher than an overall outflow capacity of the lower five outflow openings 9, and as maximum an overall outflow capacity of the lower six outflow openings 9. The peak level is at least not high enough to come out above a sixth outflow opening 9 and to discolour a fifth band of indicator substance 12'. In this exemplary embodiment outflow opening 9' is the only outflow opening where no liquid is generated from recording chamber 4 to outlet chamber 7, since a maximum accumulation level of the liquid in recording chamber 4 does not reach this level.

Carrier 11 in recording chamber 4 is covered with a liquid-tight tape (not shown) such that the indicator means comprise a surface accessible to liquid only in an area between the longitudinal wall 8 and a centre of a width line of recording chamber 4. Indicator means 10 hereby record a peak level of a liquid flow in highly reliable manner even in the case of non-optimal use of measuring device 1, such as when device 1 is in a slightly tilted position.

The exemplary embodiment of measuring device 1 according to the invention is shown in a relatively simple form, i.e. with outflow openings 9, 9' all having the same diameter and moreover being arranged in regular distribution in longitudinal wall 8. It will be apparent that diverse variants hereof can be envisaged in order to meet practical requirements, i.e. in order for instance to linearize the device, wherein the outflow from a higher outflow opening 9, 9' corresponds in each case to an equal increase in a peak level of a liquid flow.

The plastic measuring device 1 forms a flat assembly manufactured from a first sheet-like structural part from which at least one transverse wall extends by which at least the inlet, inlet chamber and recording chamber are bounded, and a second sheet-like structural part attached at least substantially liquid-tightly to the first structural part while enclosing the at least one transverse wall in at least substantially jointless manner. The first structural part and the second structural part herein comprise a thermoformed part, in particular an injection moulded part, which can be produced with a high degree of reproducibility within accurate dimensional tolerances.

Figure 2:
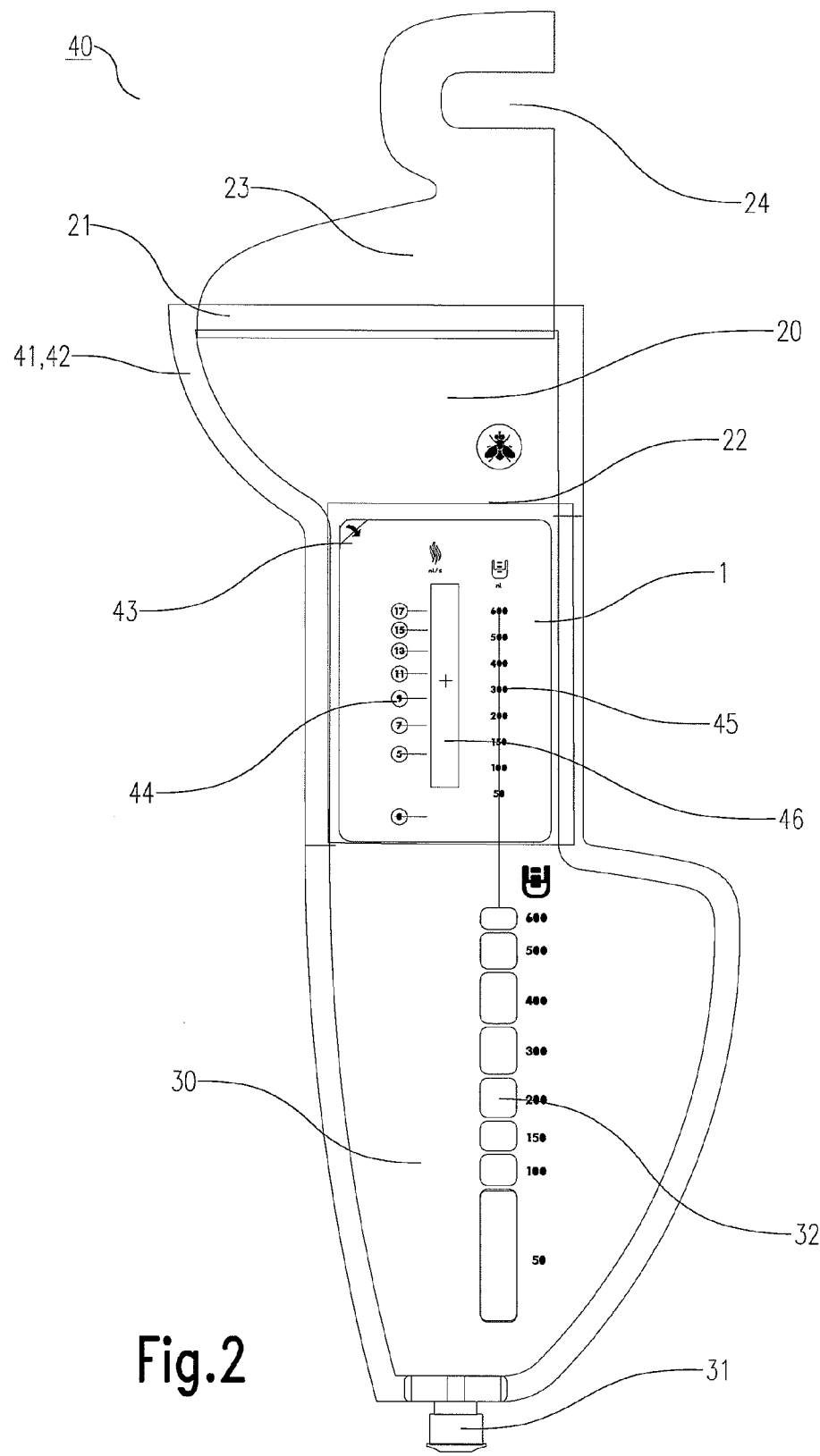
FIG. 2 shows a front view of an exemplary embodiment of a urological instrument according to the invention with a receiving device according to the invention.

FIG. 2 shows a front view of an exemplary embodiment of a urological instrument according to the invention with a receiving device according to the invention. As shown in FIG. 2, the urological instrument 40 comprises different functional components 1, 20, 30 which lie mutually in line in a folded-out, ready-to-use state of instrument 40.

The instrument 40 shown here is embodied as a disposable article formed almost completely from flexible material. For the manufacture of instrument 40 use is made here of two separate, identically shaped foil sheets 41,42 which are brought into contact with each other while enclosing a rigid edge part 21 of cardboard, plastic or other suitable, relatively rigid and resilient material. Foil sheets 41,42 are herein joined hermetically, in particular liquid-tightly, to each other on their contact surface by sealing thereof at an increased temperature and pressure as according to a defined sealing pattern.

For the purpose of its measurement function, instrument 40 comprises a separate measuring device 1 (see FIG. 1) enclosed between the two foil sheets. Measuring device 1 can thus be manufactured separately with the desired precision and optionally calibrated. During the manufacture of instrument 40 measuring device 1 can be enclosed and sealed together with edge part 21 between the two foil sheets 41, 42. The less critical parts of the device, such as a receiving device 20 and a collecting device 30, can then be formed directly by the two foil sheets 41, 42 without loss of precision, wherein the sealing pattern defines receiving device 20 and collecting device 30 between the two foil sheets 41, 42.

For the purpose of receiving a urine flow on which a peak level measurement has to be performed, instrument 40 comprises a receiving member 20 at the top. In a storage state (not shown) receiving member 20 is relatively flat and folded together with the other components 1, 30 to form a compact package. Receiving device 20 comprises a hollow receiving chamber open on both sides inside a wall, wherein the wall is manually expandable from the relatively flat storage state to an expanded, ready-to-use state. The receiving chamber herein extends between a closed upper edge 21 and a closed lower edge 22 coupled to the inlet of measuring device 1. A cross-section of the receiving chamber enclosed by upper edge 21 is significantly larger than a cross-section enclosed by lower edge 22, so that the urine flow can be admitted easily, at least substantially without wastage, to instrument 40.

The wall of the receiving chamber adjacent to upper edge 21 comprises at least a strip-like edge part 21 which is rigid and which extends at least substantially around the upper edge. From edge part 21 to lower part 22, however, the wall comprises a flexible foil. The flexible foil is formed here from an upper part of foil sheets 41,42. The foil and edge part 21 comprise an at least mutually compatible plastic, in particular the same plastic, and are attached hermetically to each other in a mutually overlapping area, in particular are sealed liquid-tightly to each other. The plastic particularly comprises a plastic from a group comprising polyethylene, polypropylene and polyester, since these are easy to process and relatively inexpensive plastics.

Edge part 21 is provided with an engaging member 23 which is connected to edge part 21 for pivoting about an at least substantially straight pivot axis and which extends distally outside upper edge 21. Engaging member 23 herein extends integrally from edge part 21 and is separated from the edge part by a linear weakening zone. Engaging member 23 can easily be grasped, on the one hand to carry receiving device 20 and on the other to open it into a ready-to-use state by manually exerting an appropriate pressure thereon. Engaging member 23 and edge part 21 herein comprise a shared pivot axis substantially transversely of the upper edge and can be folded out round the shared pivot axis. In a folded-out state the receiving device 20 leaves the receiving chamber clear on a top side for receiving the urine flow therein.

For a convenient point of engagement on which the instrument can be carried for a relatively long time, engaging member 23 comprises an engaging opening 24. The shared pivot axis is moreover interrupted by engaging in the engaging opening extending on either side of the shared pivot axis. Receiving device 21 can hereby only return to the storage state when the engaging opening is no longer being engaged.

Receiving member 20 takes an open form on its underside at lower edge 22 and debouches into an inlet of measuring device 1 shown in FIG. 1 which serves to enable assessment and recording of a peak level in the urine flow. Via respectively an inlet chamber, recording chamber and outlet chamber of measuring device 1 the inlet is in open communication with a collecting device 30 in order to receive at least a part of the urine flow therein.

Instrument 40 allows of simple use in practice by for instance placing instrument 40 obliquely in a measuring beaker in which the urine can be collected for the purpose of providing a measure of the quantity of released urine. The urine can here be released in simple manner by opening a closing member 31 which is normally in a closed position. In the present embodiment however, use is made of an embodiment wherein a collecting device 30 provided with volume indicator means 32 is already incorporated in the instrument itself. Collecting device 30 here comprises a collecting bag defined in the sealing pattern of the two foil sheets. The collecting bag connects onto measuring device 1 at an outer end opposite receiving member 20. In the storage state (not shown) the collecting bag is folded together with the rest of instrument 40 and herein covers measuring device 1. The collecting bag is preferably provided on an underside with the closing member 31. The collecting bag can be emptied easily on the underside by operating this closing member 31. It is then not necessary to release the urine by reversing instrument 40 with receiving device 20, with all the adverse consequences this would entail.

FIG. 2 further shows that receiving device 20 is provided on a front side with volume indicator means for determining the total quantity of the urine flow. On a front side of measuring device 1 are situated recording means in the form of a removable self-adhesive label 43 on which the possible measured values 44,45 of both the peak level measurement and a volume measurement are preprinted. The correct respective values are recorded in reliable manner by marking the values thereon. Label 43 can be easily detached from the instrument after use and adhered in a logbook or onto another suitable carrier so as to be made available to a doctor treating the case. Label 43 is otherwise provided with a transparent window 46 at the position of a recording area, for instance the recording chamber, of measuring device 1 so as not to adversely affect the legibility thereof. The label thus also provides an informative framing of this recording area.

It will be apparent from the above elucidation that instrument 40 is preferably embodied as disposable article, wherein it is advantageous that it be formed substantially from flexible material. This provides the option that, from the storage state in which receiving member 20, measuring device 1 and collecting device 30 are folded onto each other, the urological instrument 40 can be readily brought to the ready-to-use state shown in FIG. 2, in which these components are placed mutually in line.

Although the invention has been further elucidated with reference to only several exemplary embodiments, it will be apparent that the invention is by no means limited thereto. On the contrary, many variations and embodiments are still possible within the scope of the invention for a person with ordinary skill in the art.

The invention claimed is:
1. A urological instrument that includes a measuring device (10) for recording a peak level of a liquid flow from a user, the urological instrument comprising:
   a receiving member (20) for receiving the liquid flow;
   the measuring device (10) for recording the peak level of the liquid flow;
   a collecting device (30) for collecting said liquid flow,
   wherein said receiving member connects to said measuring device and said measuring device connects to said collecting device,
   wherein the measuring device (10) includes
   i) an inlet (2) opening into an inlet chamber (3), wherein the inlet chamber receives the liquid flow through the inlet opening;
   ii) a recording chamber (4) that communicates with the inlet chamber (3) through a passage opening (6) to allow said liquid flow to accumulate, at least temporarily, up to a level in said recording chamber, and
   an outlet chamber (7) that is adjacent said recording chamber (4),
   wherein said recording chamber is separated from said inlet opening for direct liquid communication by an intermediate wall that leaves said passage opening (6) on a side remote from said inlet opening (2);
   wherein said recording chamber comprises at least one outflow opening (9, 9') to allow a discharge of said liquid from the recording chamber into the outlet chamber up to a peak level,
   wherein said at least one outflow opening (9,9') comprises a series of outflow openings (9,9') configured to allow a partial discharge of said liquid from said recording chamber into said outlet chamber at consecutive indication levels; and indicator means provided in said recording chamber that leave an indication of said peak level, wherein the indicator means are arranged to each of said series of outflow openings to register a liquid level up one of said indication levels, wherein said measuring device comprises an at least substantially flat assembly of a first sheet-like structural part and a second sheet-like structural part that is attached at least substantially liquid-tightly to said first structural part while enclosing at least one transverse wall that defines said inlet chamber, said recording chamber and said outlet chamber, wherein said measuring device (10) is enclosed between a pair of foil sheets that are joined hermetically to each other on a mutual contact surface;

wherein said collecting device (30) is at least partially formed by and between said foil sheets, wherein said receiving member (20) is at least partially formed by and between said foil sheets, wherein said receiving device comprises a substantially hollow receiving chamber inside a wall that opens on opposites side, said wall being expandable from a relatively flat storage state to an expanded ready-to-use state in which the receiving member extends between a circumferential upper edge and a circumferential lower edge, a cross section enclosed by said upper edge being significantly larger than a cross section enclosed by said lower edge, wherein said receiving member connects at said lower edge to the inlet opening of said measuring device, wherein said receiving member carries a form-retaining rim member around said upper edge that is manually deployable from a relatively compact storage state to a deployed ready-to-use state exposing said receiving chamber inside said receiving device, and wherein said receiving device is formed by said pair of foil sheets between said rim member and said lower edge.

2. The urological instrument as claimed in claim 1, wherein said inlet chamber and said recording chamber are situated at least substantially parallel to and adjacently of each other, wherein said recording chamber extends between a first longitudinal wall (5) and a second longitudinal wall (8), wherein said first longitudinal wall (5) extends between said inlet chamber (3) and said recording chamber (4) to thereby form said intermediate wall that separates the recording chamber (4) from said inlet opening for direct liquid communication, wherein said second longitudinal wall (8) extends between said recording chamber (4) and said outlet chamber (7) to thereby separate said recording chamber (4) and said outlet chamber (7), wherein said second longitudinal wall (8) comprises a series of outflow openings (9,9') configured to allow a partial discharge of said liquid from said recording chamber into said outlet chamber at selected indication levels, and wherein indicator means are arranged to each of said series of outflow openings to register a liquid level up to said outflow opening.

3. The urological instrument as claimed in claim 2, wherein, the indicator means comprises bands of an indicator substance (12, 12') at positions of each of said series of the outflow openings, the bands of the indicator substance discolouring upon contact with the liquid so that when the liquid in the recording chamber rises to a level the same as a corresponding one of the bands of the indicator substance, an indication is given hereof, thereby giving the indication of the peak level of the liquid flow.

4. The urological instrument as claimed in claim 3, wherein the indicator means comprise a flexible carrier strip (11) on which said bands of said indicator substance are arranged.

5. The urological instrument as claimed in claim 3, wherein, the indicator means comprise a flexible paper carrier strip (11) on which said bands of said indicator substance are arranged.

6. The urological instrument as claimed in claim 4, wherein said indicator substance is attached to said carrier by means of a liquid-tight attaching means.

7. The urological instrument as claimed in claim 5, wherein said indicator substance is attached to said carrier by means of a liquid-tight attaching means.

8. The urological instrument as claimed in claim 1, wherein the device is manufactured, at least around the at least one outflow opening, from a hydrophilic material.

9. The urological instrument as claimed in claim 1, wherein at least one of the first structural part and the second structural part comprises a thermo-formed part.

10. The urological instrument as claimed in claim 1, wherein said form-retaining rim member comprises a engaging member, said receiving device and said engaging member being foldable along a shared first fold-line from said storage stage to a transition state, wherein said engaging member and said receiving device are mutually connected over a second fold-line for folding at least substantially transverse of the first fold-line to bring the receiving device in said ready-to-use state.

11. The urological instrument as claimed in claim 10, wherein the engaging member comprises a gripping opening that extends on either side of said first fold-line.

* * * * *